(12) United States Patent
Kuang et al.

(10) Patent No.: US 9,428,730 B2
(45) Date of Patent: Aug. 30, 2016

(54) COATINGS AND CULTURE MEDIA FOR PROMOTING NEUROGENESIS IN ADIPOSE TISSUE DERIVED STEM CELLS

(75) Inventors: Chenzhong Kuang, Newburgh, IN (US); Yan Xiao, Newburgh, IN (US); Zeina Jouni, Evansville, IN (US); Eduard K. Poels, Newburgh, IN (US); Dirk Hondmann, Evansville, IN (US)

(73) Assignee: Mead Johnson Nutrition Company, Glenview, IL (US)

( * ) Notice: Subject to any disclaimer, the term of this patent is extended or adjusted under 35 U.S.C. 154(b) by 0 days.

(21) Appl. No.: 13/408,490

(22) Filed: Feb. 29, 2012

(65) Prior Publication Data

US 2013/0224862 A1   Aug. 29, 2013

(51) Int. Cl.
*C12N 5/07* (2010.01)
*C12N 5/079* (2010.01)

(52) U.S. Cl.
CPC ......... *C12N 5/0618* (2013.01); *C12N 2501/11* (2013.01); *C12N 2501/115* (2013.01); *C12N 2506/1384* (2013.01); *C12N 2533/32* (2013.01); *C12N 2533/52* (2013.01)

(58) Field of Classification Search
CPC ..................... C12N 2501/11; C12N 2501/115
USPC ....................................................... 435/405
See application file for complete search history.

(56) References Cited

U.S. PATENT DOCUMENTS

2005/0214941 A1   9/2005   Bhonsale et al.
2007/0020247 A1   1/2007   Ravindran et al.

FOREIGN PATENT DOCUMENTS

| CN | 101117625 A | 2/2008 |
|---|---|---|
| WO | 2005076845 | 8/2005 |
| WO | 2006044204 | 4/2006 |
| WO | 2006102902 | 10/2006 |
| WO | 2007106200 | 9/2007 |
| WO | WO 2009097657 A1 * | 8/2009 |
| WO | 2011050476 | 5/2011 |
| WO | 2011159075 | 12/2011 |

OTHER PUBLICATIONS

Invitrogen Glutamine Product Offerings. Invitrogen Glutamine search. [retrieved on Dec. 8, 2012]. Retrieved from the internet: <http://www.invitrogen.com/search/global/searchAction.action?query=glutamine&resultsPerPage=15&show_seproductcategorynavigator=true&show_productcategorynavigator=true&show_taxonomynavigator=true&show_brandnavigator=true&show_sedocumenttypenavigator=true&mode=and&navigator=seproductcategorynavigator&modifier=Supplements>.*

Optimal Growth of Neurons and Neural Stem Cells. Invitrogen, 2009. [Retrieved on May 17, 2013]. Retrieved from the Internet: <http://www.invitrogen.com/etc/medialib/en/filelibrary/Support/BioProbes/BioProbes-60.Par.53639.File.dat/BioProbes-60-neurobasal-media.pdf>.*

Invitrogen Neurobasal Medium (1X) Liquid without Phenol Red. Datasheet [online]. Invitrogen, 2013 [Retrieved on May 17, 2013]. Retrieved from the Internet: <http://www.invitrogen.com/site/us/en/home/support/Product-Technical-Resources/media_formulation.255.html>.*

Dottori et al., "Neural differentiation of human embryonic stem cells." in Doering (ed.), Protocols for Neural Cell Culture, Springer Protocols Handbooks (Hamilton, ON, Canada, Springer, 2010), pp. 75-86.*

Invitrogen Neurobasal-A Medium (1X) Liquid. Datasheet [online]. Invitrogen, 2013 [Retrieved on Sep. 14, 2013]. Retrieved from the Internet: <http://www.lifetechnologies.com/us/en/home/technical-resources/media-formulation.253.html>.*

Invitrogen N-2 Supplement. Datasheet [online]. Invitrogen, 2013 [Retrieved on Sep. 14, 2013]. Retrieved from the Internet: https://tools.lifetechnologies.com/Content/SFS/COAPDFs/2008/390424_17502.pdf.*

Freshney, "Defined Media and Supplements." in: Culture of Animal Cells: A Manual of Basic Technique and Specialized Applications, Sixth edition (John Wiley & Sons, Inc., Hoboken, NJ, 2010), pp. 99-114.*

N2 Supplement. Datasheet [online]. ThermoFisher Scientific, 2016 [retrieved on Apr. 2, 2016]. Retrieved from the Internet: <URL: https://www.thermofisher.com/us/en/home/technical-resources/media-formulation.166.html>.*

Androutsellis-Theotokis, A., et al., "Generating Neurons from Stem Cells," Methods in Molecular Biology, vol. 438, Feb. 1, 2008, pp. 31-38.

Murashov, A., et al., "17B-Estradiol enhances neuronal differentiation of mouse embryonic stem cells," FEBS Letters 569 (2004) 165-168.

Bottenstein, J, et al. "Growth of a rat neuroblastoma cell line in serum-free supplemented medium," Proc. Natl. Acad. Sci. USA, vol. 76, No. 1, pp. 514-517, Jan. 1979.

SLI Data Sheet, Media, N2 Supplement, MED-268, 100x concentrate 5mL.

PAA Reagent Series, N2 Supplement, F005-004, 100 x concentrate. life technologiesTM, Technical Resources—Media Formulations, N2-Supplement 100 x liquid, catalog No. 17502048, www.invtrogen.com/site/us/en/home/support/Product-Technical-Resources/media_formulation.166.html.

(Continued)

*Primary Examiner* — Kara Johnson
(74) *Attorney, Agent, or Firm* — Patterson Intellectual Property Law, P.C.; James R. Cartiglia; Timothy L. Capria (57) ABSTRACT

Provided herein are coatings for stem cell cultureware comprising poly-L-ornithine and bovine fibronectin and methods for preparing coated stem cultureware comprising contacting cultureware with poly-L-ornithine and contacting the cultureware with bovine fibronectin. Also provided are stem cell culture media comprising epidermal growth factor, beta-fibroblast growth factor and $N_2$ supplement.

10 Claims, 6 Drawing Sheets

(56) References Cited

OTHER PUBLICATIONS

Alan, "Human/Mouse/Rate Neural Lineage Functional Identification Kit," Dec. 22, 2011.

Ashjian, P., et al., "In Vitro Differentiation of Human Processed Lipoaspirate Cells into Early Neural Progenitors," Plast. Reconstr. Surg. 111: 1922-1931, 2003.

Huang, T., et al., "Neuron-like Differentiation of Adipose-Derived Stem Cells From Infant Piglets in Vitro," J Spinal Cord Med. 2007;30:S35-S40.

Kawakita, E., et al., "Docosahexaenoic Acid Promotes Neurogenesis In Vitro and In Vivo," Neuroscience 139 (2006) 991-997.

Safford, K., et al., "Neurogenic differentiation of murine and human adipose-derived stromal cells," Biochemical and Biophysical Research Communications 294 (2002) 371-379.

Lee, J., et al., "Tumor stem cells derived from glioblastomas cultured in bFGF and EGF more closely mirror the phenotype and genotype of primary tumors than do serum-cultured cell lines," Cancer Cell 9, 391-403, May 2006.

Podgornyi, O., et al., "Formation of Neuroepithelial Structures in Culture of Neural Stem Cells from Human Brain," Cell Technologies in Biology and Medicine, No. 3, Sep. 2005.

* cited by examiner

COATINGS AND CULTURE MEDIA FOR PROMOTING NEUROGENESIS IN ADIPOSE TISSUE DERIVED STEM CELLS

TECHNICAL FIELD

The present disclosure relates to coatings for stem cell cultureware, methods for preparing coated stem cell cultureware and culture media. The coatings, cultureware and media are useful for promoting neurogenesis in adipose-derived stem cells, including human adipose-derived stem cells.

BACKGROUND

Brain nutrients have become increasingly important additives in the diets of infants, children and pregnant and lactating women because of their ability to promote early brain development. Additionally, compounds useful for treating neurodegenerative disease or brain injury are continuously being sought. Neuro-toxic compounds, such as environmental, industrial or dietary toxins, need to be identified in order to remove or reduce exposure to such compounds. Methods for discovering such nutrients and toxins are often extremely time consuming and inefficient. Accordingly, there is a need to provide a reliable, consistent, and fast method for identifying compounds having neurological development benefits. Additionally, there is need to identify compounds that are neurologically harmful.

It has been demonstrated that stem cells, such as adipose-derived stem cells (ADSCs), can be differentiated into multiple mature cell phenotypes, including neuronal cells, in a reproducible manner. In particular, this has been demonstrated in human adipose-derived stem cells (hADSCs). hADSCs are a useful research tool because they are readily available from commercial resources or liposuction procedures, and they do not involve the same potential controversies that arise from the use of embryonic stem cells. Furthermore, hADSCs are easily obtained from an individual patient, thus providing an opportunity for personalized medicine. Accordingly, there is a need to provide procedures for promoting neurogenesis in ADSCs, and more particularly, to provide suitable cultureware and media for promoting neurogenesis in ADSCs.

BRIEF SUMMARY

One aspect of the disclosure relates to a coating for stem cell cultureware comprising poly-L-ornithine and bovine fibronectin. The stem cells may be adipose-derived stem cells, such as human adipose derived stem cells. In some embodiments, the coating advantageously promotes cell attachment, cell growth, and/or neurogenesis.

Another aspect of the disclosure relates to cultureware for stem cells, the cultureware having coated thereon a coating capable of promoting neurogenesis, such as a coating comprising poly-L-ornithine and bovine fibronectin.

Another aspect of the disclosure relates to a method for preparing coated stem cell cultureware, comprising: contacting cultureware with a solution of poly-L-ornithine, and contacting the cultureware with a solution of bovine fibronectin. The contacting steps may be performed in any order, or simultaneously or substantially simultaneously.

The concentration of the poly-L-ornithine in the poly-L-ornithine solution is, in some embodiments, in a range of about 0.1 to about 1000 µg/mL. The step of contacting the cultureware with the solution of poly-L-ornithine may be performed for an amount of time sufficient to dispose the poly-L-ornithine on at least one surface of the cultureware, for example for about 10 minutes to about 12 hours. The step of contacting the cultureware with the solution of poly-L-ornithine may be performed at an ambient temperature or elevated temperature, for example about 20 to about 45° C.

In some embodiments, the concentration of bovine fibronectin in the bovine fibronectin solution is in a range of about 0.1 to about 1000 µg/mL. The step of contacting the cultureware with the solution of bovine fibronectin may be performed for an amount of time sufficient to dispose the bovine fibronectin on at least one surface of the cultureware, for example for about 10 minutes to about 12 hours. The step of contacting the cultureware with the solution of bovine fibronectin may be performed at a temperature of, for example, about 15 to about 40° C.

Another aspect of the disclosure relates to stem cell cultureware coated with bovine fibronectin and poly-L-ornithine prepared according to any of the methods disclosed herein.

Still another aspect of the disclosure relates to a medium for stem cell culture comprising: a neural basal medium, epidermal growth factor (EGF), basic fibroblast growth factor (b-FGF), and N2 supplement. For example, the medium can comprise a neural basal medium with about 1 to about 100 ng/mL of EGF, about 1 to about 100 ng/mL of b-FGF, and about 1× of N2 supplement. In some embodiments, the medium further comprises L-glutamine, for example about 0.1 to about 10 mM of L-glutamine. The aforementioned medium may advantageously promote or support neurogenesis.

Also provided herein are systems for culturing stem cells, comprising:
stem cells;
cultureware for stem cells, the cultureware having coated thereon a coating comprising poly-l-ornithine and bovine fibronectin; and
a culture medium.
In some embodiments, the system further comprises a priming medium.

BRIEF DESCRIPTION OF THE DRAWINGS

FIG. 2 is a diagram depicting an extended neuronal differentiation platform (ENDP) according to an embodiment of the present disclosure. hADSCs are cultured in a suitable priming medium for up to three days. The priming medium is then replaced with a suitable culture medium (differentiation medium) and an appropriate amount of a candidate compound and cultured for 1 to 5 days. The hADSCs are then evaluated to determining the extent of neurogenesis.

DETAILED DESCRIPTION

One aspect of the present disclosure relates cultureware for stem cells, such as ADSCs, having disposed on at least one surface a coating comprising poly-L-ornithine and bovine fibronectin. While not being bound by any particular theory, it is believed that the cultureware coating described herein mimics the in vivo environment of the central nervous system, maximizes cellular neuronal differentiation activity, and enhances cellular attachment in ADSCs. Thus, the coating in some embodiments promotes neurogenesis.

"Neurogenesis" refers to the differentiation, generation or proliferation of neural cells from stem or progenitor cells in vitro or in vivo. The extent of neurogenesis can be determined by a variety of techniques known in the art, such as by observing morphological changes in the cells. Any method for cellular analysis or visualization is suitable for use in the present methods. For example, morphological changes in the ADSCs may be observed using a microscopic technique, such as phase contrast microscopy. Morphological changes that indicate neurogenesis include, but are not limited to, shrinkage of cytoplasm and the presence of neurites, axons and dendrites. In other embodiments, the extent of neurogenesis is determined by observing cellular biomarkers indicative of neurogenesis, such as by using biomarker expression experiments. Examples of such biomarkers include, but are not limited to, proteins such as neurofilaments, myelin basic protein, microtubule associated protein 2 (MAP2), nestin, β-III tubulin, glial fibrillar acidic protein (GFAP), S100 (a calcium binding protein), CNPase and GABA receptor. Biomarker expression experiments include, but are not limited to, cell staining studies.

Another aspect of the disclosure relates to a method of preparing coated stem cell cultureware comprising: contacting cultureware with a solution of poly-L-ornithine and contacting the cultureware with a solution of bovine fibronectin. The contacting steps may be performed in any order, simultaneously, or substantially simultaneously. For example, in certain embodiments, the cultureware is contacted with the poly-L-ornithine prior to the bovine fibronectin. In other embodiments, the cultureware is contacted with the poly-L-ornithine after the bovine fibronectin, and in yet other embodiments, the poly-L-ornithine and bovine fibronectin are contacted with the cultureware simultaneously or substantially simultaneously. The steps of contacting may be performed on one surface of the cultureware or on multiple surfaces of the cultureware.

The poly-L-ornithine and bovine fibronectin are in concentrations sufficient to dispose the proteins on at least one surface of the cultureware. For example, the poly-L-ornithine solution may be an aqueous solution with a poly-L-ornithine concentration in a range of about 0.1 to about 1000 μg/mL, about 0.1 to about 500 μg/mL, about 1 to about 500 μg/mL, about 1 to about 100 μg/mL, about 1 to about 50 μg/mL or about 15 to about 20 μg/mL.

The solution of bovine fibronectin may be in an aqueous solution with a concentration in a range of about 0.1 to about 1000 μg/mL, about 0.1 to about 500 μg/mL, about 0.1 to about 100 μg/mL, about 0.1 to about 50 μg/mL, about 0.1 to about 20 μg/mL or about 1 to about 5 μg/mL. The bovine fibronectin solution, can be a buffer, such as a phosphate buffer. For example, the solution of bovine fibronectin may be prepared by combining commercially available bovine fibronectin or aqueous solution of bovine fibronectin (such as in cell culture grade water) with a suitable buffer, such as Dubellco's Phosphate Buffered Saline (DPBS).

The step of contacting the solution of poly-L-ornithine with the cultureware, or the at least one surface of the cultureware, can be performed by any method known in the art. In some embodiments, the step of contacting the solution of poly-L-ornithine with the cultureware is performed by rinsing or pouring the solution the over the cultureware, soaking or immersing the cultureware in the solution, mixing or agitating the solution with or around the cultureware, spraying the cultureware with the solution, sonicating the cultureware in the solution, or any combination thereof.

The step of contacting the solution of poly-L-ornithine with the cultureware is performed for a period of time sufficient to dispose the poly-L-ornithine on at least one surface of the cultureware, such as about 10 minutes to about 12, about 30 minutes to about 6 hours, or about 1 hour.

In some embodiments, the poly-L-ornithine contacting step is carried out at an ambient or elevated temperature. For example, the step of contacting the solution of poly-L-ornithine with the cultureware can be performed at a temperature of about 20 to about 45° C., about 25 to about 40° C., about 30 to about 40° C., or about 37° C.

The step of contacting the solution of bovine fibronectin with the cultureware can be performed by any method known in the art. In an embodiment, the step of contacting the solution of bovine fibronectin with the cultureware is performed by rinsing or pouring the solution the over the cultureware, soaking or immersing the cultureware in the solution, mixing or agitating the solution with or around the cultureware, spraying the cultureware with the solution, sonicating the cultureware in the solution, or any combination thereof.

The step of contacting the solution of bovine fibronectin with the cultureware is performed for a period of time sufficient to dispose the bovine fibronectin on at least one surface of the cultureware, for example for about 10 minutes to about 12 hours, about 30 minutes to about 6 hours, or about 1 hour.

The step of contacting the solution of bovine fibronectin with the cultureware can be performed at an ambient or elevated temperature. In some embodiments, the temperature about 15 to about 45° C., about 15 to about 35° C., about 15 to about 30° C., about 23° C., or about room temperature.

In certain embodiments, the methods for preparing coated stem cell cultureware further comprise a washing step. The washing step may be with water or an aqueous solution, such as an aqueous buffer, e.g., DPBS solution. The cultureware can be washed one or more times prior to the contacting with the poly-L-ornithine or fibronectin solution. The cultureware also can be washed one or more times in between the contacting steps one or more times after the contacting steps. In some embodiments, the cultureware is dried after the contacting and optional washing steps.

Another aspect of the disclosure relates to coated stem cell cultureware prepared by any of the aforementioned methods. In an embodiment, the coated stem cell cultureware promotes neurogenesis in ADSCs, such as hADSCs. The cultureware to be coated can be any vessel suitable for culturing stem cells, including but not limited to multiwall plates, dishes, slides, tubes, and the like, and may be coated one surface or a plurality of surfaces.

Another aspect of the disclosure relates to media useful for culturing stem cells, such as ADSCs, and more particularly, hADSCs. In some embodiments, the media are capable of promoting neurogenesis. For example, the culture medium may be capable of guiding the ADSCs to differentiate into neuronal cell types. In some embodiments, the medium comprises a neural basal medium, epidermal growth factor (EGF), basic fibroblast growth factor (b-FGF), N2 supplement and L-glutamine, which are available from commercial sources, such as Invitrogen. For example, the neural basal medium can be Neurobasal™ Medium, available from Invitrogen, which may comprise the ingredients listed in Table 1:

TABLE 1

Neurobasal ™ Medium

| Components | Molecular Weight | Concentration (mg/L) | mM |
|---|---|---|---|
| Amino Acids | | | |
| Glycine | 75 | 30 | 0.4 |
| L-Alanine | 89 | 2 | 0.0225 |
| L-Arginine hydrochloride | 211 | 84 | 0.398 |
| L-Asparagine-H2O | 150 | 0.83 | 0.00553 |
| L-Cysteine | 121 | 31.5 | 0.26 |
| L-Histidine hydrochloride-H2O | 210 | 42 | 0.2 |
| L-Isoleucine | 131 | 105 | 0.802 |
| L-Leucine | 131 | 105 | 0.802 |
| L-Lysine hydrochloride | 183 | 146 | 0.798 |
| L-Methionine | 149 | 30 | 0.201 |
| L-Phenylalanine | 165 | 66 | 0.4 |
| L-Proline | 115 | 7.76 | 0.0675 |
| L-Serine | 105 | 42 | 0.4 |
| L-Threonine | 119 | 95 | 0.798 |
| L-Tryptophan | 204 | 16 | 0.0784 |
| L-Tyrosine | 181 | 72 | 0.398 |
| L-Valine | 117 | 94 | 0.803 |
| Vitamins | | | |
| Choline chloride | 140 | 4 | 0.0286 |
| D-Calcium pantothenate | 477 | 4 | 0.00839 |
| Folic Acid | 441 | 4 | 0.00907 |
| Niacinamide | 122 | 4 | 0.0328 |
| Pyridoxine hydrochloride | 204 | 4 | 0.0196 |
| Riboflavin | 376 | 0.4 | 0.00106 |
| Thiamine hydrochloride | 337 | 4 | 0.0119 |
| Vitamin B12 | 1355 | 0.0068 | 0.000005 |
| i-Inositol | 180 | 7.2 | 0.04 |
| Inorganic Salts | | | |
| Calcium Chloride (CaCl2) (anhyd.) | 111 | 200 | 1.8 |
| Ferric Nitrate (Fe(NO3)3"9H2O) | 404 | 0.1 | 0.000248 |
| Magnesium Chloride (anhydrous) | 95 | 77.3 | 0.814 |
| Potassium Chloride (KCl) | 75 | 400 | 5.33 |
| Sodium Bicarbonate (NaHCO3) | 84 | 2200 | 26.19 |
| Sodium Chloride (NaCl) | 58 | 3000 | 51.72 |

TABLE 1-continued

Neurobasal ™ Medium

| Components | Molecular Weight | Concentration (mg/L) | mM |
|---|---|---|---|
| Sodium Phosphate monobasic (NaH2PO4—H2O) | 138 | 125 | 0.906 |
| Zinc sulfate (ZnSO4—7H2O) | 288 | 0.194 | 0.000674 |
| Other Components | | | |
| D-Glucose (Dextrose) | 180 | 4500 | 25 |
| HEPES | 238 | 2600 | 10.92 |
| Sodium Pyruvate | 110 | 25 | 0.227 |

N2 supplement may be purchased from Invitrogen. The Invitrogen N2 supplement may comprise the following ingredients:

TABLE 2

N2 Supplement

| Components | Molecular Weight | Concentration (mg/L) | mM |
|---|---|---|---|
| Proteins | | | |
| Human transferrin (Holo) | 10000 | 10000 | 1 |
| Insulin recombinant full chain | 5807.7 | 500 | 0.0861 |
| Other components | | | |
| Progesterone | 314.47 | 0.63 | 0.002 |
| Putreseine | 161 | 1611 | 10.01 |
| selenite | 173 | 0.52 | 0.00301 |

In certain embodiments, the culture medium comprises a neural basal medium with EGF, b-FGF, N2 supplement and L-glutamine added in appropriate concentrations. For example, the medium may comprise about 1 to about 100, about 5 to about 50, about 10 to about 25 or about 20 ng/mL of EGF. The medium further comprises about 1 to about 100 ng/mL, about 5 to about 50, about 10 to about 25, or about 20 ng/mL of b-FGF. The N2 supplement may be present in the medium at a concentration of about 1x, and L-glutamine may be present in an amount of about 0.1 to about 10 mM, about 1 to about 5 mM, or about 2 mM.

The cultureware coatings and stem cell media disclosed herein are useful in methods for identifying neurogenesis-modulating compounds using ADSCs. A "neurogenesis-modulating compound" refers to a compound that affects neurogenesis, either by promoting or inhibiting neurogenesis. Thus, in some embodiments, neurogenesis-modulating compounds promote neurogenesis ("neurogenesis-promoting compounds"), while in other embodiments, the neurogenesis-modulating compounds inhibit or reduce neurogenesis ("neurogenesis-inhibiting compounds"). Compounds identified as promoting neurogenesis may advantageously be used as supplements in the diets of infants, children and pregnant and lactating mothers in order to promote and support early brain development. These compounds also may be useful in treating neurodegenerative diseases or neurological injuries. Compounds identified as inhibiting neurogenesis may be potential toxins to be avoided or removed from the diets and environments of infants, children, and pregnant and lactating women. These compounds also may interfere with the treatment or healing of neurological diseases or injuries. Thus, neurogenesis-inhibiting compounds may also be avoided in the diets and environments of individuals suffering from neurological disease or injury.

A "candidate compound" refers to any compound to be tested for neurogenesis-modulating properties using the methods described herein. The candidate compounds include, without limitation, naturally occurring substances, synthetic compounds, or extracts, such as extracts of plant or animal tissues, fungi or bacteria. The candidate compound may be tested alone or it may be tested in combination with other candidate compounds or known neurogenesis-modulating compound in order to observe synergistic effects or to achieve higher throughput screening of compounds. Accordingly, in some embodiments, the medium further comprises an amount of the candidate compound ranging from about 0.1 nM to about 10 mM, or 1 nM to about 1 mM.

In certain embodiments, the culturing medium is substantially free of serum or, preferably, completely free of serum. A culture medium substantially free of serum refers to medium having less than about 10% serum, more particularly less than about 2% or less than about 1% serum; in some embodiments, substantially free of serum refers to less than about 0.5% serum. A culture medium completely free of serum has no serum. While not being bound by any particular theory, it is believed that serum may contain inconsistent amounts of growth factors, which may impact the extent of neurogenesis. Accordingly, serum-free media eliminate the effects of serum on the extent of neurogenesis. Neurogenesis observed in ADSCs cultured in low serum or serum-free media can thus be attributed to the candidate compound rather than the presence of serum.

The aforementioned media are useful in a rapid neuronal differentiation platform ("RNDP"). The RNDP may advantageously be used to rapidly screen large numbers of potential neurogenesis modulating compounds. Compounds may screened singly, or in combination with other compound to achieve high through put results. Compounds identified in the RNDP may be further investigated using an extended platform, if desired. In some embodiments, the culture medium used in the RNDP comprises a neural basal medium, EGF, β-FGF, N2 supplement and L-glutamine.

An extended neuronal differentiation protocol ("ENDP") further comprises a priming step. While not being bound by any particular theory, it is believed that priming the ADSCs allows for improved neuronal morphology. Accordingly, in some embodiments, the ADSCs are primed prior to culturing in the presence of a candidate compound. For example, the ADSCs can be primed for about 1 to about 5 days in a suitable priming medium prior to culturing with the candidate compound. In other embodiments, the ADSCs are primed for about 1 to about 3 days, or for about 3 days. While not being bound by any particular theory, it is believed that priming the ADSCs prior to culturing provides additional time for the ADSCs to develop into neuronal lineages.

In some embodiments, the priming medium comprises a neural basal medium (such as Neurobasal Medium™ from Invitrogen), with suitable concentrations of EGF, b-FGF, and N2 supplement. Suitable concentrations of EGF include about 1 to about 100 ng/mL, about 5 to about 50, about 10 to about 25 or about 20 ng/mL. Suitable concentrations of b-FGF include about 1 to about 100, about 5 to about 50, about 10 to about 25, or about 20 ng/mL of b-FGF. The N2 supplement may be present in the medium at a concentration of about 1x. The priming medium may be substantially free of serum or completely free of serum. A priming medium substantially free of serum refers to medium having less than about 10% serum, for example less than about 2% or 0.1% serum, while a culture medium completely free of serum has no serum. Furthermore, the priming medium may be free of or substantially free of the candidate compound.

In embodiments wherein the ADSCs are primed prior to being cultured in the presence of a candidate compound, the ADSCs are subsequently cultured in a suitable culture medium for about 1 to about 5 days. In other embodiments, the ADSCs are cultured for about 1 to about 3 days, or for about 3 days. After priming, the priming medium is removed and a culturing medium is added to the ADSCs. The culture medium comprises, for example, MesenPRO complete, available from Invitrogen. The culture medium may further comprise a suitable amount of the candidate compound, for example about 0.1 nM to about 10 mM, or 1 nM to about 1 mM of the candidate compound.

In some embodiments, the aforementioned screening methods further comprise providing a negative control culture of ADSCs for comparison to the candidate compound. Thus, the method may further comprise culturing ADSCs in the absence of the candidate compound, determining the extent of neurogenesis in the ADSCs cultured in the absence of the candidate compound, and comparing the extent of neurogenesis in the ADSCs cultured in the presence of the candidate compound to the extent of neurogenesis of the ADSCs cultured in the absence of the candidate compound. An increase in the extent of neurogenesis in the ADSCs cultured in the presence of the candidate compound compared to the extent of neurogenesis in the ADSCs cultured in the absence of the candidate compound indicates that the candidate compound is a neurogenesis-promoting compound. On the other hand, a decrease in the extent of neurogenesis in the ADSCs cultured in the presence of the candidate compound compared to the extent of neurogenesis in the ADSCs cultured in the absence of the candidate compound indicates that the candidate compound is a neurogenesis-inhibiting compound.

In other embodiments, the method further comprises providing a positive control culture. Thus, the method may further comprise culturing ADSCs in the presence a known neurogenesis-promoting compound, and determining the extent of neurogenesis in the ADSCs cultured in the presence of the neurogenesis-promoting compound. For example, DHA is known to promote early brain development and may be used as a positive control. Accordingly, the method may further comprise culturing ADSCs in the presence of DHA. An increase in the extent of neurogenesis in the ADSCs cultured in the presence of the candidate compound compared to the extent of neurogenesis in the ADSCs cultured in the presence of DHA indicates that the candidate compound is a superior neurogenesis-promoting compound than DHA.

During neurogenesis, the ADSCs may differentiate into neuronal cells, precursors to neuronal cells, and cells having neuronal properties. Accordingly, the extent of neurogenesis can be determined by observing morphological changes in the cells. Changes in cell morphology that are indicative of neurogenesis include, but are not limited to, shrinkage of cell cytoplasm, formation of a neurite, formation of a dendrite-like projection, formation of an axon, or a combination thereof. Other changes in cell morphology indicative of neurogenesis include development of a morphology that resembles bi-polar, tri-polar and multi-polar neuronal cells.

Changes in cell morphology can be observed by a microscopic technique, such as by phase contrast microscopy. Phase contrast microscopy images of the ADSCs may be multiple times during the culturing of the ADSCs. For example, images may be taken prior to culturing with the candidate compound, and one or more times after addition of the candidate compound, such as three hours after, and then once daily thereafter.

Changes in cellular biomarkers occur during neurogenesis. Thus, in some embodiments, a cellular expression study for neuronal markers is used to determine the extent of neurogenesis. Examples of such biomarkers include, but are not limited to, proteins such as neurofilaments, myelin basic protein, nestin, β-III tubulin, glial fibrillar acidic protein, S100 (a calcium binding protein), CNPase and GABA receptor.

In some embodiments, the stem cells are ADSCs, hADSCs. hADSCs can be maintained in culture and readily passaged to provide multiple sub-cultures. Furthermore, hADSCs are readily available because they can be isolated from human adipose tissue collected during routine liposuction procedures and cryopreserved from primary cultures. In an embodiment, hADSCs can be obtained from an individual patient. The hADSCs thus obtained can be used in the methods described herein to screen a candidate compound for individualized use. Accordingly, personalized and optimized nutrition, drug treatment, or sensitivity to neurotoxins can be achieved.

Another aspect of the disclosure relates to a system for identifying a neurogenesis-modulating compound, comprising: cultureware comprising coating that mimics the central nervous system and a culture medium. In some embodiments, the coating comprises bovine fibronectin and poly-L-ornithine. In systems useful in the RNDP, the culture medium the culture medium comprises a neural basal medium, EGF, b-FGF, N2 supplement, and L-glutamine. Systems useful in the ENDP, further comprise a priming medium, such as a medium comprising a neural basal medium, EGF, b-FGF, $N_2$ supplement, and a culture medium comprising MesenPRO Complete. In some embodiments, the system further includes stem cells, such as ADSC's.

EXAMPLES hADSCs

The hADSCs used in the following procedures are purchased from commercial resources and grown in the maintenance media consisting of Complete MesenPRO RS medium with supplement and L-glutamine. The subculture of hADSCs is performed when cell culture reaches confluence. To passage hADSCs, the following procedure is used: i) aspirate the Complete MesenPRO RS medium from the cells; ii) rinse the surface area of the cell layer with Dulbecco's phosphate buffered saline (DBPS) buffer by adding the DPBS to the side of the vessel opposite the attached cell layer and rocking the vessel back and forth several times; iii) remove the DPBS by aspiration and discard; iv) detach the cells by adding a sufficient volume of pre-warmed trypsin-EDTA solution without phenol red to cover the cell layer; v) incubate at 37° C. for approximately 7 minutes; vi) observe the cells under a microscope to determine if additional incubation is needed; vii) add 3 mL of the maintenance media to the plate, mix the cell suspension, add the suspension to a 15 mL centrifuge tube and centrifuge at 210 g for 5 minutes; viii) determine the total number of cells and percent viability using a hemacytometer; ix) add Complete MesenPRO RS medium to each vessel so that the final culture volume is 0.2 mL-0.5 mL per $cm^2$; x) seed the cells by adding the appropriate volume of cells to each vessel and incubate at 37° C., 5% $CO_2$ and 90% humidity; and xi) three or four days after seeding, completely remove the medium and replace with an equal volume of Complete MesenPRO RS medium.

Coating

Before seeding the passaged hADSCs on fresh culture plates, the surfaces of the culture ware are washed with sterile DPBS solution three times, followed by multiple rinses with sterile water. The first layer of coating is poly-L-ornithine. The coating is prepared by adding about 15 to about 20 µg/mL of poly-L-ornithine and incubating at 37° C. for one hour. The plate is washed three times with DPBS, 15 minutes per wash. The second layer of coating is bovine plasma fibronectin. The fibronectin is diluted in DPBS from stock to 1:1000 and 500 µL is added to each well. The plate is left at room temperature for one hour. One final wash with 500 µL per well of DPBS is performed and the plate is used immediately.

Medium hADSCs can be maintained in an undifferentiated state or guided to differentiate using different culture media. Certain culture media are capable of guiding ADSCs to differentiate into neuronal cells. Exemplary media are set forth in Tables 3, 4 and 5.

TABLE 3

Serum-free RNDP medium

| component | Final concentration |
|---|---|
| neural basal medium | 500 mL |
| EGF | 20 ng/mL |
| b-FGF | 20 ng/mL |
| N2 supplement | 1× |
| L-glutamine | 2 mM |

TABLE 4

Serum-free ENDP priming medium

| component | Final concentration |
|---|---|
| neural basal medium | 500 mL |
| EGF | 20 ng/mL |
| bFGF | 20 ng/mL |
| N2 supplement | 1× |

TABLE 5

ENDP differentiation medium

| component | Final concentration |
|---|---|
| MesenPRO complete | 500 mL |

RNDP Protocol

Two independent screening protocols are described, designated as rapid neuronal differentiation platform (RNDP) and extended neuronal differentiation platform (ENDP). The RNDP protocol provides rapid screening of large numbers of candidate compounds in a relatively short period of time. RNDP allows the rapid identification of compounds that either promote or inhibit neurogenesis, or that have no effect on neurogenesis. The RNDP may be followed by an ENDP in order to further investigate and confirm the results.

The subculture media of the hADSCs described above is removed from the culture dish, and the dish is then gently washed with 5-10 mL of sterile DPBS. The DPBS is removed and 1.5 mL of trypsin-EDTA is added to completely cover the cell layer. The dish is placed back in the incubator for seven minutes. The plate is then gently tapped to detach cells completely. 3 mL of the maintenance media is added to the plate, and the cell suspension is mixed and added to 15 mL centrifuge tube. The desired cell density ($1 \times 10^4$ cells/well) is taken to another 15 mL tube and placed to centrifuge at 210 g for 5 minutes. The cell pellet is resuspended in an appropriate volume of pre-warmed serum-free rapid neuronal differentiation medium as set forth in Table 1 and seeded onto each well of tissue culture plate. The candidate compounds for each well are added sequentially. The plate is put back into the incubator. The effects of the candidate compounds are quickly and easily observed using phase contrast microscopy images, which are usually taken once immediately before treatment, three hours post treatment and each day thereafter for three days. With a fast turnover time, the best results typically occur within 36 hours. After images are collected, data analysis and comparison is made to determine the effectiveness of each compound or mixture of compounds in modulating neurogenesis. Neuronal differentiation is determined by observing neuronal morphology. Some changes in the cells include shrinking of the cytoplasm, formation of axons and dendrite-like cytoplasmic projections. These changes begin with the cytoplasm of hADSCs retracting toward the nucleus to form contracted cell bodies with cytoplasmic extensions. Cells eventually develop a morphology that resembles bi-polar, tri-polar, and multi-polar neuronal cells.

ENDP Protocol

The ENDP protocol provides a method for further investigation of the results of the RNDP and also allows additional time for priming the hADSCs for further differentiation into various neuronal cell lineages. While not being bound by any particular theory, the priming drives transdifferentiation of the hADSCs from mesoderm lineages to neural ectoderm.

The hADSCs are seeded on culture plates with coated surfaces and grown in the serum-free ENDP priming medium (see table 2) for at least 72 hours. The priming medium is removed and neuronal differentiation medium added (see Table 3) in the presence or absence of at least one candidate compound. The cultures are then incubated for an extended period of time for further neuronal development. After three days of incubation, the cells are examined under microscope for morphological changes. The percentage and length of neurites can be measured by using open software of Image J with an appropriate plug-in. The cells can further be studied for various neuronal markers to further confirm neuronal differentiation.

Discovery of Brain Nutrients

The purpose of this investigation is to determine the neurogenesis effect of various nutrients (candidate compounds) using both RNDP and ENDP platforms. The candidate compounds are tested individually and compared to the positive control, docosahexaenoic acid (DHA), and the negative control. Pre-warmed serum-free medium contains Neural Basal medium with L-glutamine, 20 ng/mL of βFGF, 20 ng/mL of EGF and $N_2$ supplement. The candidate compound is added to individual wells at various concentrations in the serum-free medium. The candidate compounds are selected from the group consisting of ARA, EPA (cis-5,8,11,14,17-eicosapentaenoic acid) and resveratrol. The compounds are tested individually and compared to the positive control, docosahexaenoic acid (DHA), and the negative control. The experiments are repeated in triplicate. The nutrients found to promote neurogenesis or demonstrate use as a medicament are screened in various combinations. These experiments are also repeated in triplicate.

Figure 1:
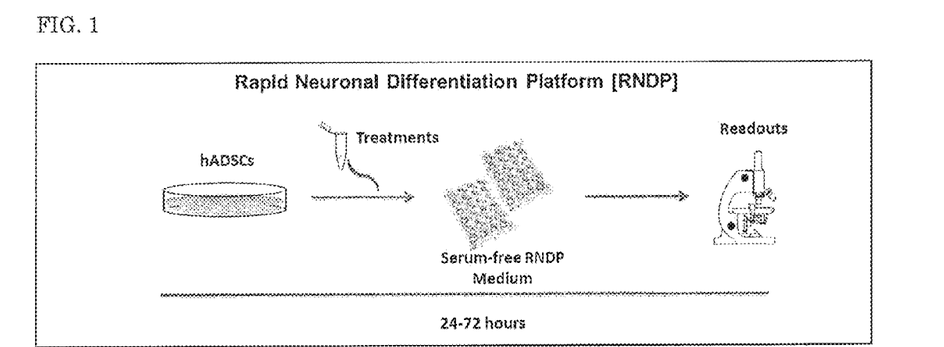
FIG. 1 is a diagram depicting a rapid neuronal differentiation platform (RNDP) according to an embodiment of the present disclosure. hADSCs are cultured in a suitable culture medium and an appropriate amount a candidate compound (treatment) for 24-72 hours. The hADSCs are then evaluated to determining the extent of neurogenesis.
Figure 2:
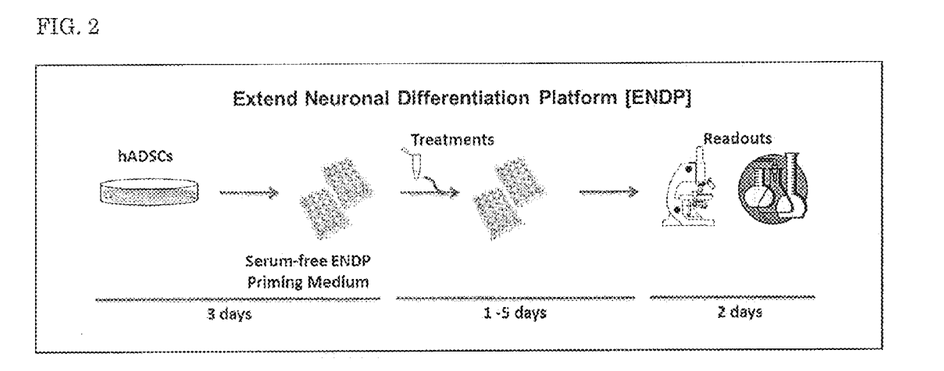
Figure 3A:
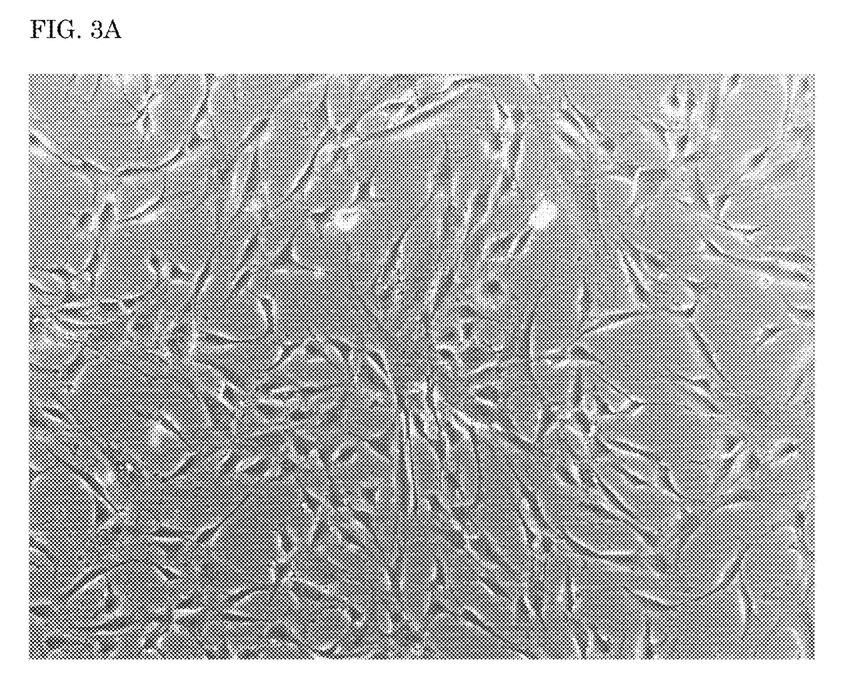
FIG. 3A depicts a phase contrast image of a ADSC's in a control experiment.
Figure 3B:
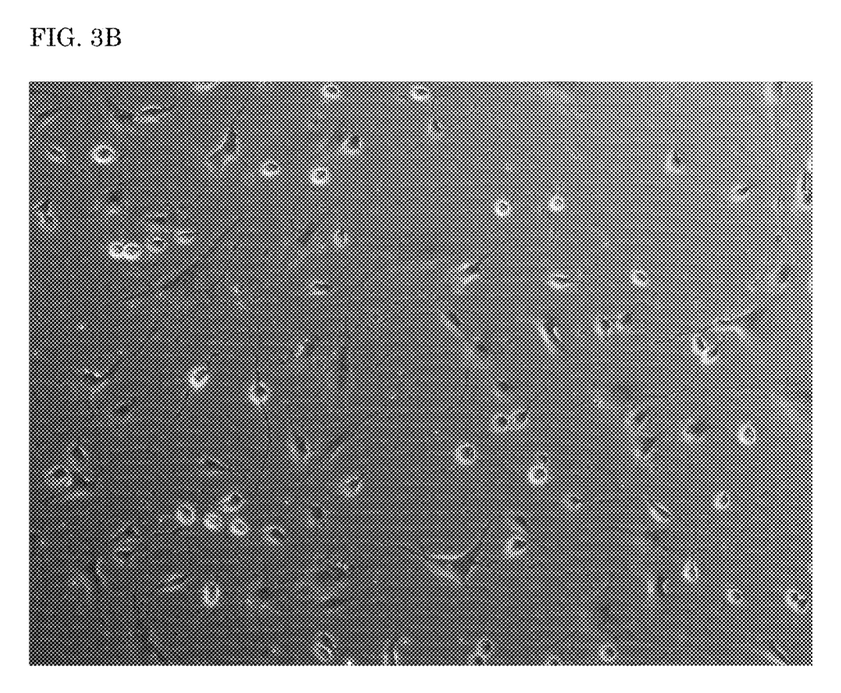
FIG. 3B depicts a phase contrast image of ADSC's post brain nutrient treatment.
Figure 4A:
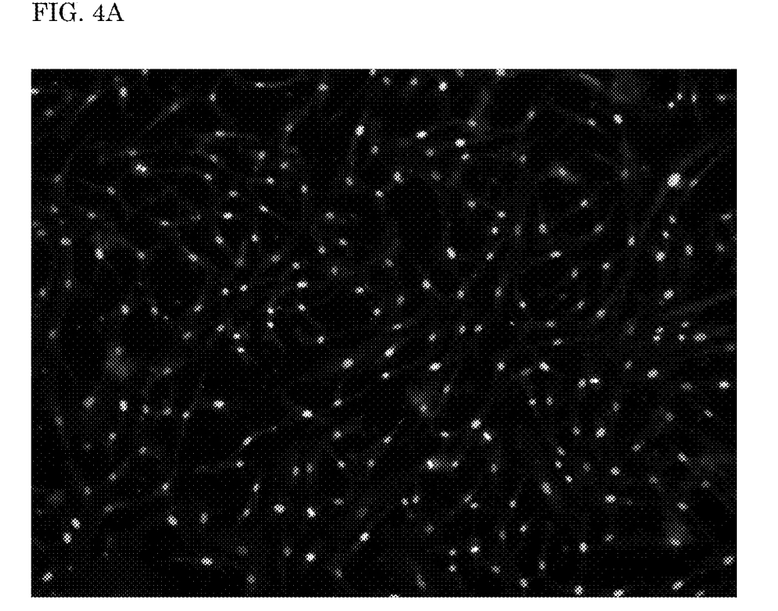
FIG. 4A is a control image from a cellular expression study in which cells are stained with an antibody against microtubule-associated protein 2 (MAP2), a neuronal marker.
Figure 4B:
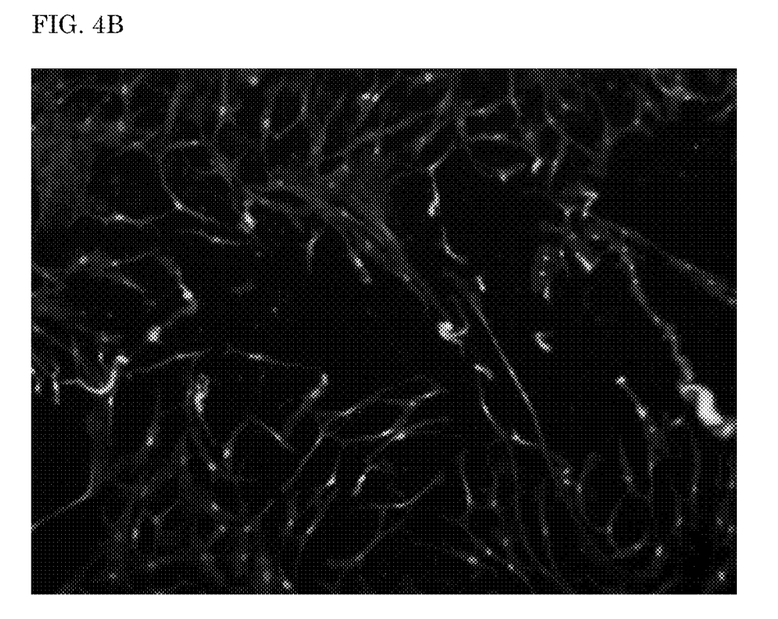
FIG. 4B is a post brain nutrient treatment image in the MAP2 expression study. Red fluorescence (indicated by the white streaks) demonstrates the expression of MAP2.
Figure 5A:
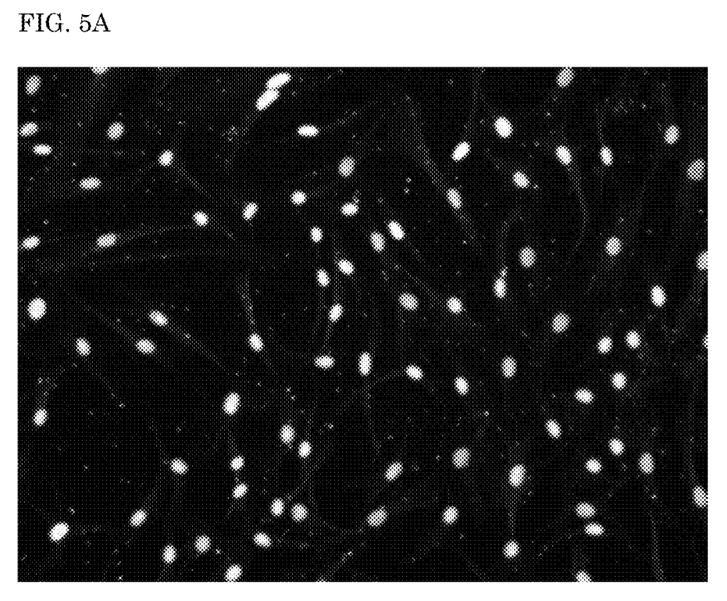
FIG. 5A is a control image from a cellular expression study in which cells are stained with an antibody against nestin, a neuronal marker.
Figure 5B:
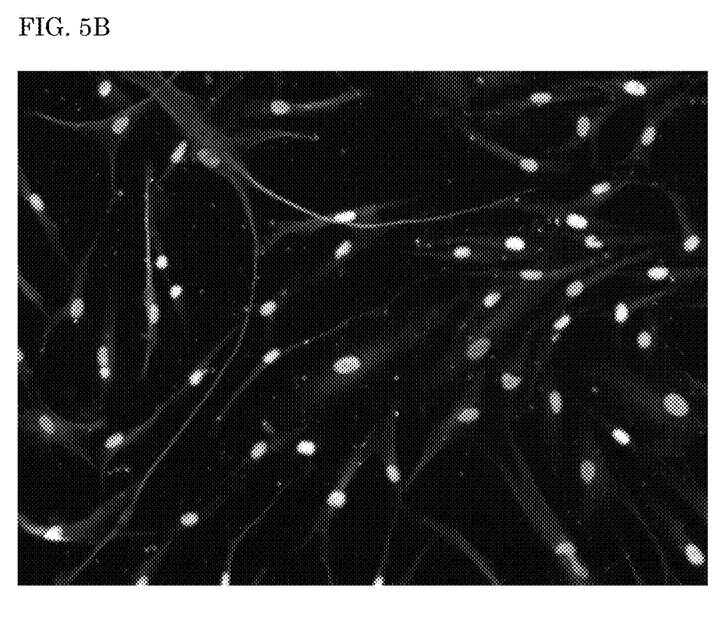
FIG. 5B is a post brain nutrient treatment image in the nestin expression study. Red fluorescence (indicated by the white streaks) demonstrates the expression of nestin.
Figure 6A:
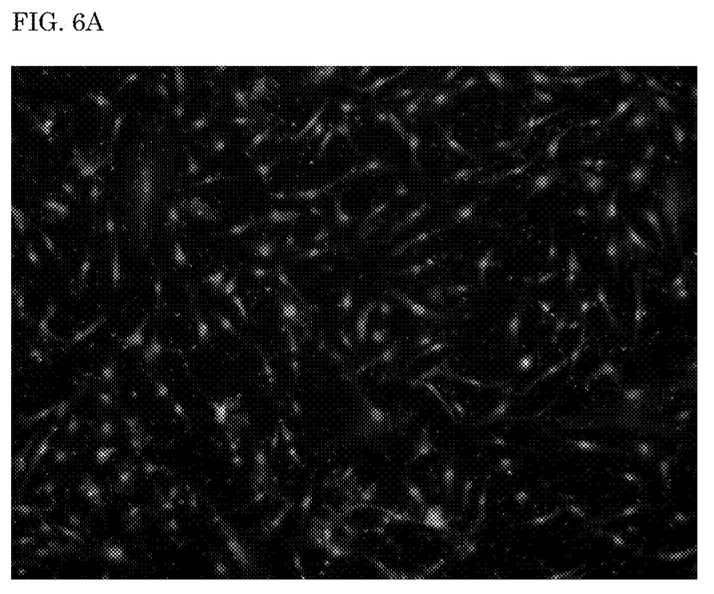
FIG. 6A is a control image from a cellular expression study in which cells are stained with an antibody against glial fibrillary acidic protein (GFAP), a neuronal marker.
Figure 6B:
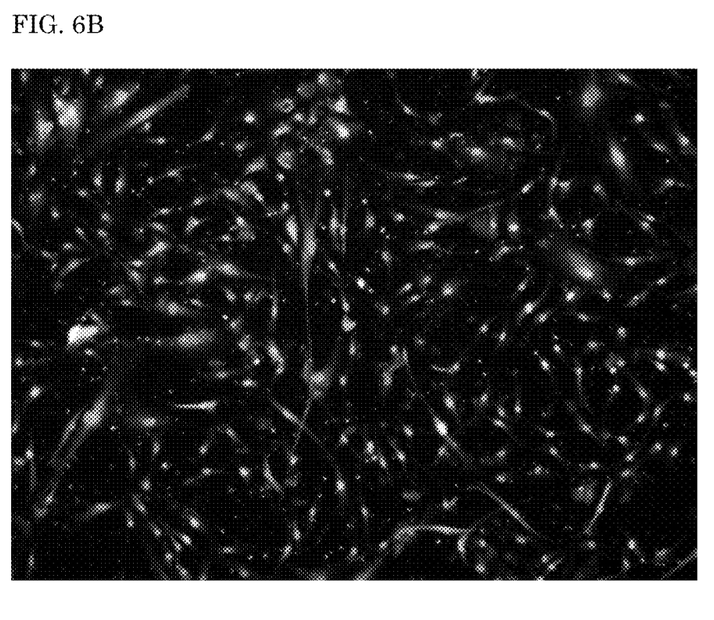
FIG. 6B is a post brain nutrient treatment image in the GFAP expression study. Red fluorescence (indicated by the white streaks) demonstrates the expression of GFAP.
Figure 7A:
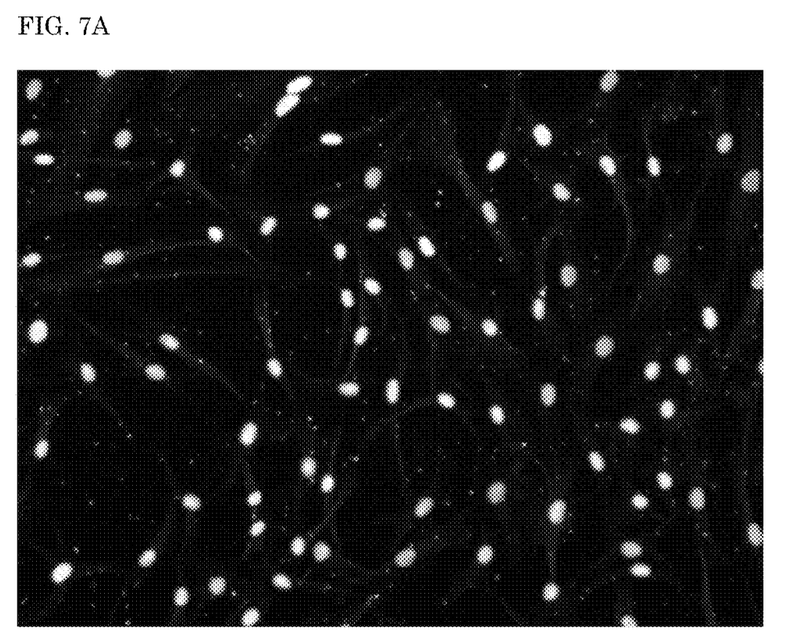
FIG. 7A is a control image from a cellular expression study in which cells are stained with an antibody against beta III tubulin, a neuronal marker.
Figure 7B:
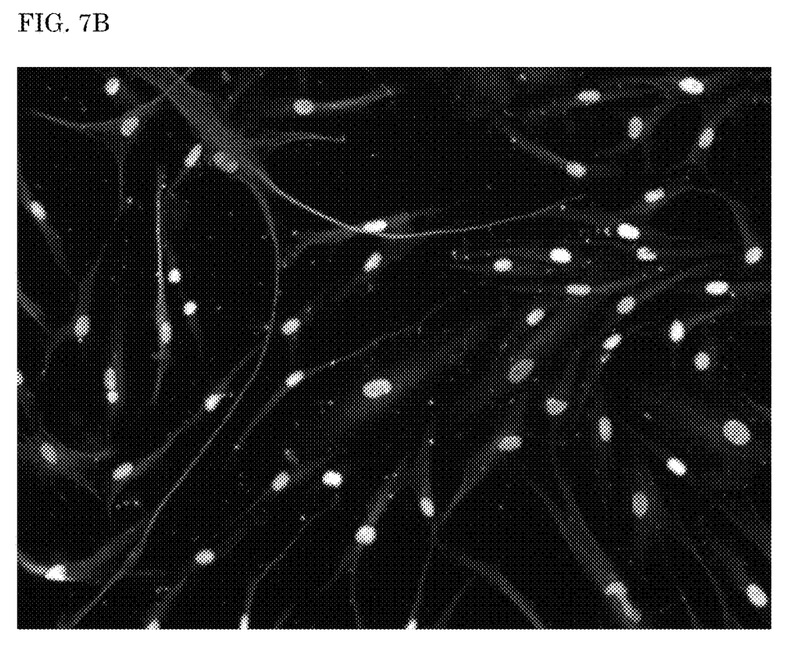
FIG. 7B is a post brain nutrient treatment image in the beta III tubulin expression study. Red fluorescence (indicated by the white streaks) demonstrates the expression of beta III tubulin.

The effects of the candidate compounds are easily and quickly observed under phase contrast microscopy for up to one week with images usually taken once immediately before treatment with the candidate compound, three hours post treatment, and each day thereafter for three days. With a fast turnover time, the best results typically occur within 36 hours. After images are collected, data analysis and comparison is made to determine the effectiveness of each compound or combination of compounds in promoting neurogenesis. Neuronal differentiation is determined by neuronal morphology. Some of these changes include shrinkage of the cytoplasm, and formation of axons and dendrite-like cytoplasmic projections (neurites). These changes begin with the cytoplasm of hADSCs retracting towards the nucleus to form contracted cell bodies with cytoplasmic extensions. Cells eventually develop a morphology that resembles bi-polar, tri-polar and multi-polar neuronal cells (see FIGS. 3A and 3B).

The effects of the candidate compounds are also observed using various neuronal marker expression studies. Specifically cells stained with antibodies against MAP2, nestin, GFAP and beta III tubulin demonstrate expression (as indicated by red fluorescence) of these markers after treatment with brain nutrients, as depicted in FIGS. 4A-7B.

Of the above candidate compounds, resveratrol, ARA, EPA, cholesterol and DHA are examples of compounds that effectively promote neurogenesis. The test concentrations and effective concentrations are depicted in table 6:

TABLE 6

Examples of compounds identified as effectively promoting neurogenesis

| Compound | Testing range | Effective range |
| --- | --- | --- |
| DHA | 1 nM-1 mM | 5-20 μM |
| ARA | 1 nM-1 mM | 2-10 μM |
| EPA (Cis-5,8,11,14,17-Eicosapentaenoic acid) | 1 nM-1 mM | 10-40 μM |
| Cholesterol | 1 μM-10 μM | 50-200 μM |
| Resveratrol | 100 nM-50 mM | 2 μM-20 mM |

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional ingredients, components or limitations described herein.

As used herein, the term "about" should be construed to refer to both of the numbers specified in any range. Any reference to a range should be considered as providing support for any subset within that range.

We claim:

1. A neuronal differentiation medium for culturing human adipose derived stem cells consisting of:
a neural basal medium, wherein the neural basal medium consists of glycine, L-alanine, L-arginine, L-asparagine, L-cysteine, L-histidine, L-isoleucine, L-leucine, L-lysine, L-methionine, L-phenylalanine, L-proline, L-serine, L-threonine, L-tryptophan, L-tyrosine, L-valine, choline, D-calcium pantothenate, folic acid, niacinamide, pyridoxine hydrochloride, riboflavin, thiamine hydrochloride, vitamin B12, i-inositol, calcium chloride, ferric nitrate, magnesium chloride, potassium chloride, sodium bicarbonate, sodium chloride, sodium phosphate, zinc sulfate, dextrose, 4-(Z-hydroxyethyl)-1-piperazineethanesulfonic acid, sodium pyruvate, epidermal growth factor (EGF) at a concentration about 1 to about 100 ng/mL, b-fibroblast growth factor (b-FGF) at a concentration of about 1 to 100 ng/mL, and N2 supplement at a concentration of about 1x, wherein the medium promotes neurogenesis, and wherein the neuronal differentiation medium is substantially free of serum.

2. The medium of claim 1, wherein the N2 supplement comprises human transferrin, full chain recombinant insulin, progesterone, putrescine, and selenite.

3. The medium of claim 1, wherein the medium promotes neurogenesis by inducing one or more morphological changes in one or more cells exposed to the medium, wherein the one or more morphological changes observed include at least one selected from the group consisting of shrinkage of the cytoplasm, promoting neurite formation, promoting axon formation, promoting dendrite formation, and combinations thereof.

4. The medium of claim 3, wherein the one or more cells exposed to the medium are adipocyte derived stem cells.

5. The medium of claim 4, wherein the one or more cells exposed to the medium are human adipocyte derived stem cells.

6. A neuronal differentiation medium for culturing human adipose derived stem cells consisting of:

a neural basal medium, wherein the neural basal medium consists of from the group consisting of glycine, L-alanine, L-arginine, L-asparagine, L-cysteine, L-histidine, L-isoleucine, L-leucine, L-lysine, L-methionine, L-phenylalanine, L-proline, L-serine, L-threonine, L-tryptophan, L-tyrosine, L-valine, choline, D-calcium pantothenate, folic acid, niacinamide, pyridoxine hydrochloride, riboflavin, thiamine hydrochloride, vitamin B12, i-inositol, calcium chloride, ferric nitrate, magnesium chloride, potassium chloride, sodium bicarbonate, sodium chloride, sodium phosphate, zinc sulfate, dextrose, 4-(Z-hydroxyethyl)-1-piperazineethanesulfonic acid, sodium pyruvate, epidermal growth factor (EGF) at a concentration about 1 to about 100 ng/mL, b-fibroblast growth factor (b-FGF) at a concentration of about 1 to 100 ng/mL, N2 supplement at a concentration of about 1x, and L-glutamine at a concentration of about 0.1 to about 10 mM, wherein the medium promotes neurogenesis, and wherein the neuronal differentiation medium is substantially free of serum.

7. The medium of claim 6, wherein the N2 supplement comprises human transferrin, full chain recombinant insulin, progesterone, putrescine, and selenite.

8. The medium of claim 6, wherein the medium promotes neurogenesis by inducing one or more morphological changes in one or more cells exposed to the medium, wherein the one or more morphological changes observed include at least one selected from the group consisting of shrinkage of the cytoplasm, promoting neurite formation, promoting axon formation, and promoting dendrite formation.

9. The medium of claim 8, wherein the one or more cells exposed to the medium are adipocyte derived stem cells.

10. The medium of claim 9, wherein the one or more cells exposed to the medium are human adipocyte derived stem cells.

* * * * *